(12) United States Patent
Griffith et al.

(10) Patent No.: US 9,925,385 B2
(45) Date of Patent: Mar. 27, 2018

(54) TIMING CHANNEL CIRCUITRY FOR CREATING PULSES IN AN IMPLANTABLE STIMULATOR DEVICE

(71) Applicant: Boston Scientific Neuromodulation Corporation, Valencia, CA (US)

(72) Inventors: Paul J. Griffith, Moorpark, CA (US); Goran N. Marnfeldt, Valencia, CA (US); Jordi Parramon, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 15/289,809

(22) Filed: Oct. 10, 2016

(65) Prior Publication Data

US 2017/0021181 A1    Jan. 26, 2017

Related U.S. Application Data

(60) Continuation of application No. 14/858,554, filed on Sep. 18, 2015, now Pat. No. 9,468,771, which is a
(Continued)

(51) Int. Cl.
*A61N 1/37* (2006.01)
*A61N 1/372* (2006.01)
*A61N 1/36* (2006.01)

(52) U.S. Cl.
CPC ..... *A61N 1/37264* (2013.01); *A61N 1/36125* (2013.01); *A61N 1/372* (2013.01); *A61N 1/37252* (2013.01)

(58) Field of Classification Search
CPC .............. A61N 1/0534; A61N 1/36067; A61N 1/36082; A61N 1/36139; A61N 1/36146;
(Continued)

(56) References Cited

U.S. PATENT DOCUMENTS 4,407,288 A * 10/1983 Langer ................. A61N 1/3622
607/4
4,690,145 A   9/1987 King-Smith et al.
(Continued)

FOREIGN PATENT DOCUMENTS

JP    61-290964    12/1986

OTHER PUBLICATIONS

Ba A et al: "Multi-waveforms generator dedicated to selective and continuous stimulations of the bladder", A Proceedings of the 25th. Annual International Conference of the IEEE Engineering in Medicine and Biology Society. Cancun, Mexico, Sep. 17-21, 2003; [Annual International Conference of the IEEE Engineering in Medicine and Biology Society. EMBS] , NE, vol. 2, Sep. 17, 2003.
(Continued)

*Primary Examiner* — Rex R Holmes
(74) *Attorney, Agent, or Firm* — Lewis, Reese & Nesmith, PLLC (57) ABSTRACT

Timing channel circuitry for controlling stimulation circuitry in an implantable stimulator is disclosed. The timing channel circuitry comprises a addressable memory. Data for the various phases of a desired pulse are stored in the memory using different numbers of words, including a command indicative of the number of words in the phase, a next address for the next phase stored in the memory, and a pulse width or duration of the current phase, control data for the stimulation circuitry, pulse amplitude, and electrode data. The command data is used to address through the words in the current phase via the address bus, which words are sent to a control register for the stimulation circuitry. After the duration of the pulse width for the current phase has passed, the stored next address is used to access the data for the next phase stored in the memory.

19 Claims, 9 Drawing Sheets

Related U.S. Application Data continuation of application No. 14/636,380, filed on Mar. 3, 2015, now Pat. No. 9,144,687, which is a division of application No. 13/847,676, filed on Mar. 20, 2013, now Pat. No. 9,008,790.

(60) Provisional application No. 61/654,603, filed on Jun. 1, 2012, provisional application No. 61/639,814, filed on Apr. 27, 2012.

(58) Field of Classification Search
CPC .............. A61N 1/3622; A61N 1/37217; A61N 1/3925; A61N 1/3962
See application file for complete search history.

(56) References Cited

U.S. PATENT DOCUMENTS

| | | | |
|---|---|---|---|
| 5,603,726 | A | 2/1997 | Schulman et al. |
| 7,024,246 | B2 | 4/2006 | Acosta et al. |
| 7,177,698 | B2 | 2/2007 | Klosterman et al. |
| 7,444,181 | B2 | 10/2008 | Shi et al. |
| 7,483,748 | B2 | 1/2009 | Torgerson et al. |
| 7,539,538 | B2 | 5/2009 | Parramon et al. |
| 7,890,182 | B2 | 2/2011 | Parramon et al. |
| 8,131,377 | B2 | 3/2012 | Shi et al. |
| 2005/0065575 | A1 | 3/2005 | Dobak |
| 2006/0173493 | A1* | 8/2006 | Armstrong ......... A61N 1/36053 607/2 |
| 2007/0100399 | A1 | 5/2007 | Parramon et al. |
| 2008/0319497 | A1 | 12/2008 | Griffith et al. |
| 2009/0024184 | A1 | 1/2009 | Sun et al. |
| 2010/0211132 | A1 | 8/2010 | Nimmagadda et al. |
| 2011/0230936 | A1* | 9/2011 | Jensen ............... A61N 1/36067 607/62 |
| 2012/0092032 | A1 | 4/2012 | Shi et al. |
| 2012/0095519 | A1 | 4/2012 | Parramon et al. |
| 2012/0095529 | A1 | 4/2012 | Parramon et al. |

OTHER PUBLICATIONS

Kuanfu Chen et al: "Highly programmable 1 e 1-23 digital controller for high-density epi-retinal prosthesis", Proceedings of the 31st Annual International Conference of the IEEE Engineering in Medicine and Biology Soci ety: Engineering the Future of Biomedicine, EMBC 2009, IEEE, Sep. 3, 2009.

International Search Report and Written Opinion regarding application No. PCT/US2013/033111 dated Jun. 6, 2013.

* cited by examiner

| | Pre-Pulse | | | |
|---|---|---|---|---|
| addr(1) | cmd1 | addr(5) | $pw_{pp}$ | |
| addr(2) | $cntl_{pp}$ | | $amp_{pp}$ | |
| addr(3) | E1='1';100% | E2='0';100% | E3=0 | E4=0 |
| addr(4) | E5=0 | E6=0 | E7=0 | E8=0 |
| | Phase 1 | | | |
| addr(5) | cmd1 | addr(9) | $pw_{p1}$ | |
| addr(6) | $cntl_{p1}$ | | $amp_{p1}$ | |
| addr(7) | E1='0';100% | E2='1';100% | E3=0 | E4=0 |
| addr(8) | E5=0 | E6=0 | E7=0 | E8=0 |
| | Inter-phase | | | |
| addr(9) | cmd0 | addr(10) | $pw_{ip}$ | |
| | Phase 2 | | | |
| addr(10) | cmd1 | addr(14) | $pw_{p2}$ | |
| addr(11) | $cntl_{p2}$ | | $amp_{p2}$ | |
| addr(12) | E1='1';100% | E2='0';100% | E3=0 | E4=0 |
| addr(13) | E5=0 | E6=0 | E7=0 | E8=0 |
| | Passive Recovery | | | |
| addr(14) | cmd2 | addr(16) | $pw_{pr}$ | |
| addr(15) | $cntl_{pr}$ | | $amp_{p2}=0$ | |
| | Quiet | | | |
| addr(16) | cmd0 | addr(1) | $pw_q$ | |

| | Phase 1-1 | | |
|---|---|---|---|
| addr(1) | cmd1 | addr(5) | pw=1ms |
| addr(2) | cntl$_{p1}$ | | amp=3mA |
| addr(3) | E1='0';100% | E2='1';100% | E3=0 | E4=0 |
| addr(4) | E5=0 | E6=0 | E7=0 | E8=0 |

202

| | Phase 1-2 | | |
|---|---|---|---|
| addr(5) | cmd1 | addr(9) | pw=1ms |
| addr(6) | cntl$_{p1}$ | | amp=3.5mA |
| addr(7) | E1='0';100% | E2='1';100% | E3=0 | E4=0 |
| addr(8) | E5=0 | E6=0 | E7=0 | E8=0 |

⋮

| | Phase 1-10 | | |
|---|---|---|---|
| addr(37) | cmd1 | addr(41) | pw=1ms |
| addr(38) | cntl$_{p1}$ | | amp=7.5mA |
| addr(39) | E1='0';100% | E2='1';100% | E3=0 | E4=0 |
| addr(40) | E5=0 | E6=0 | E7=0 | E8=0 |

TIMING CHANNEL CIRCUITRY FOR CREATING PULSES IN AN IMPLANTABLE STIMULATOR DEVICE

CROSS REFERENCE TO RELATED APPLICATIONS

This is a continuation application of U.S. patent application Ser. No. 14/858,554, filed Sep. 18, 2015 (U.S. Pat. No. 9,468,771), which is a continuation application of U.S. patent application Ser. No. 14/636,380, filed Mar. 3, 2015 (U.S. Pat. No. 9,144,687), which is a divisional application of U.S. patent application Ser. No. 13/847,676, filed Mar. 20, 2013 (U.S. Pat. No. 9,008,790), which was a non-provisional application claiming priority to U.S. Provisional Patent Application Ser. Nos. 61/654,603, filed Jun. 1, 2012, and 61/639,814, filed Apr. 27, 2012. Priority is claimed to these applications, and they are all incorporated herein by reference in their entireties.

FIELD OF THE INVENTION

The present invention relates generally to implantable medical devices, and more particularly to improved timing channel circuitry for creating pulses in an implantable stimulator device.

BACKGROUND

Implantable stimulation devices generate and deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The description that follows will generally focus on the use of the invention within a Spinal Cord Stimulation (SCS) system, such as that disclosed in U.S. Pat. No. 6,516,227. However, the present invention may find applicability in any implantable stimulator.

Figures 1A, 1B:
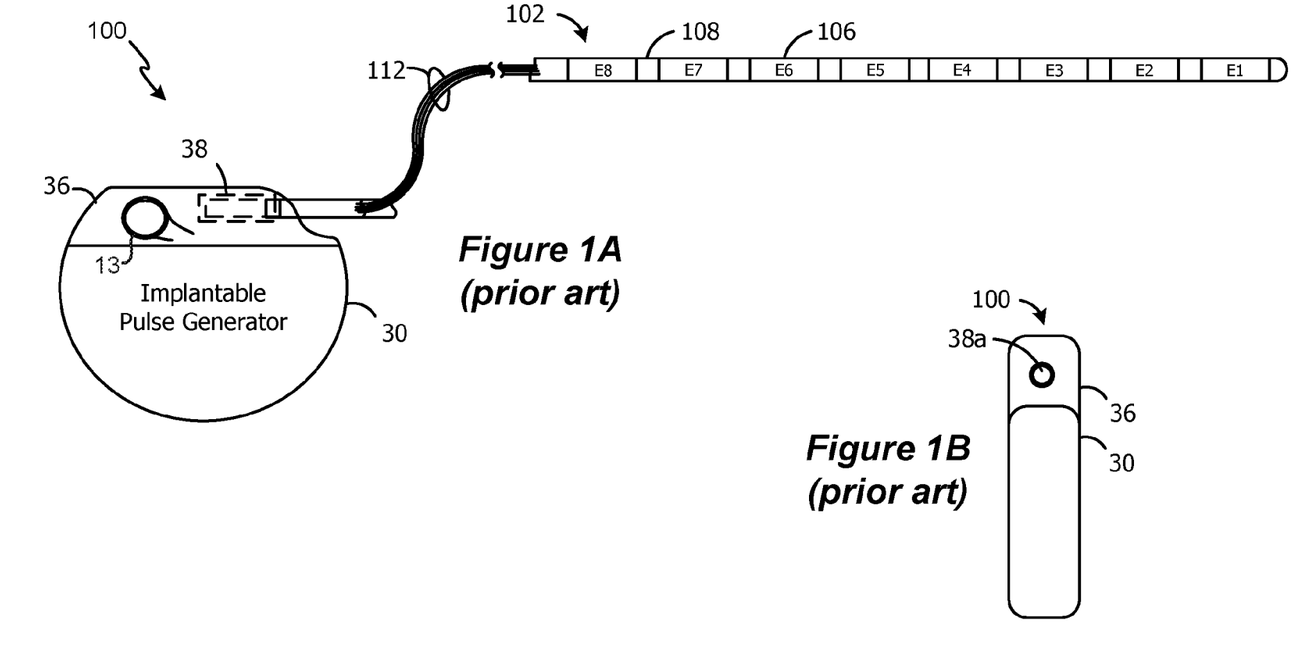
FIGS. 1A-1B show an implantable pulse generator (IPG), and an electrode array coupled to the IPG in accordance with the prior art.

As shown in FIGS. 1A and 1B, a SCS system typically includes an Implantable Pulse Generator (IPG) 100, which includes a biocompatible device case 30 formed of a conductive material such as titanium for example. The case 30 typically holds the circuitry and a battery for powering the IPG, although IPGs can also be powered via external RF energy and without a battery. The IPG 100 includes at least one electrode array 102 containing several electrodes 106. The electrodes 106 are carried on a flexible body 108, which also houses the individual electrode leads 112 coupled to each electrode. In the illustrated embodiment, there are eight electrodes on array 102, labeled $E_1$-$E_8$, although the number of arrays and electrodes is application specific and therefore can vary. The array 102 couples to the IPG 100 using a lead connector 38, which is fixed in a non-conductive header material 36, and which can comprise an epoxy for example. A communication coil 13 allows for telemetry of data to and from the IPG 100 from a device external to the patient, as is well known. An additional coil may be present to allow the battery to be recharged from an external device, as is also well known.

Figure 2A:
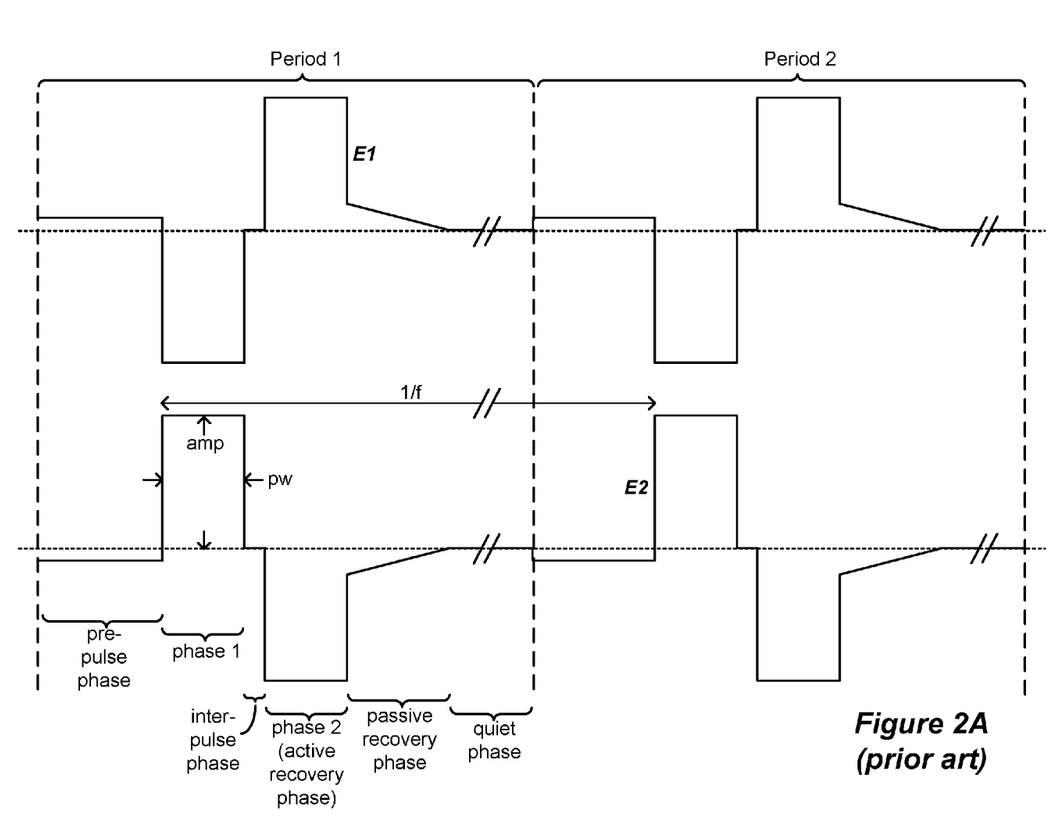
FIGS. 2A-2C illustrate example pulses created by the prior art IPG 100 of FIG. 1, and the timing channel circuitry used to send pulse parameters to stimulation circuitry.
Figure 2B:
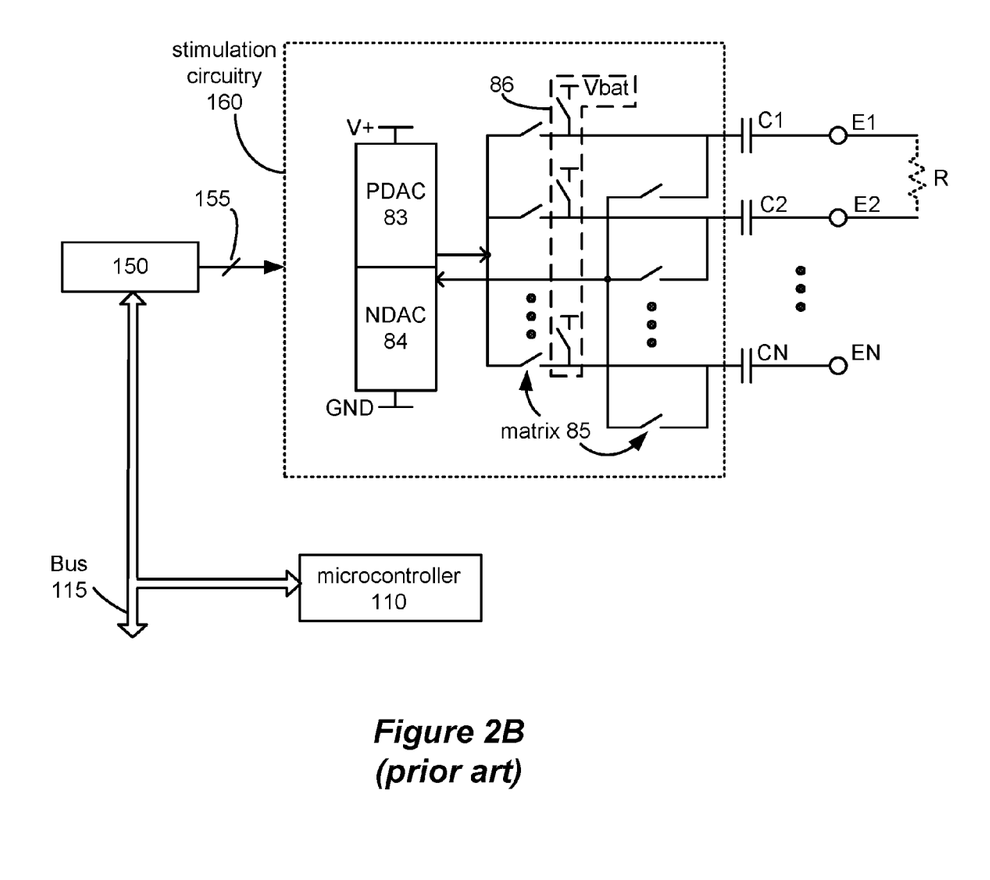
Figure 2C:
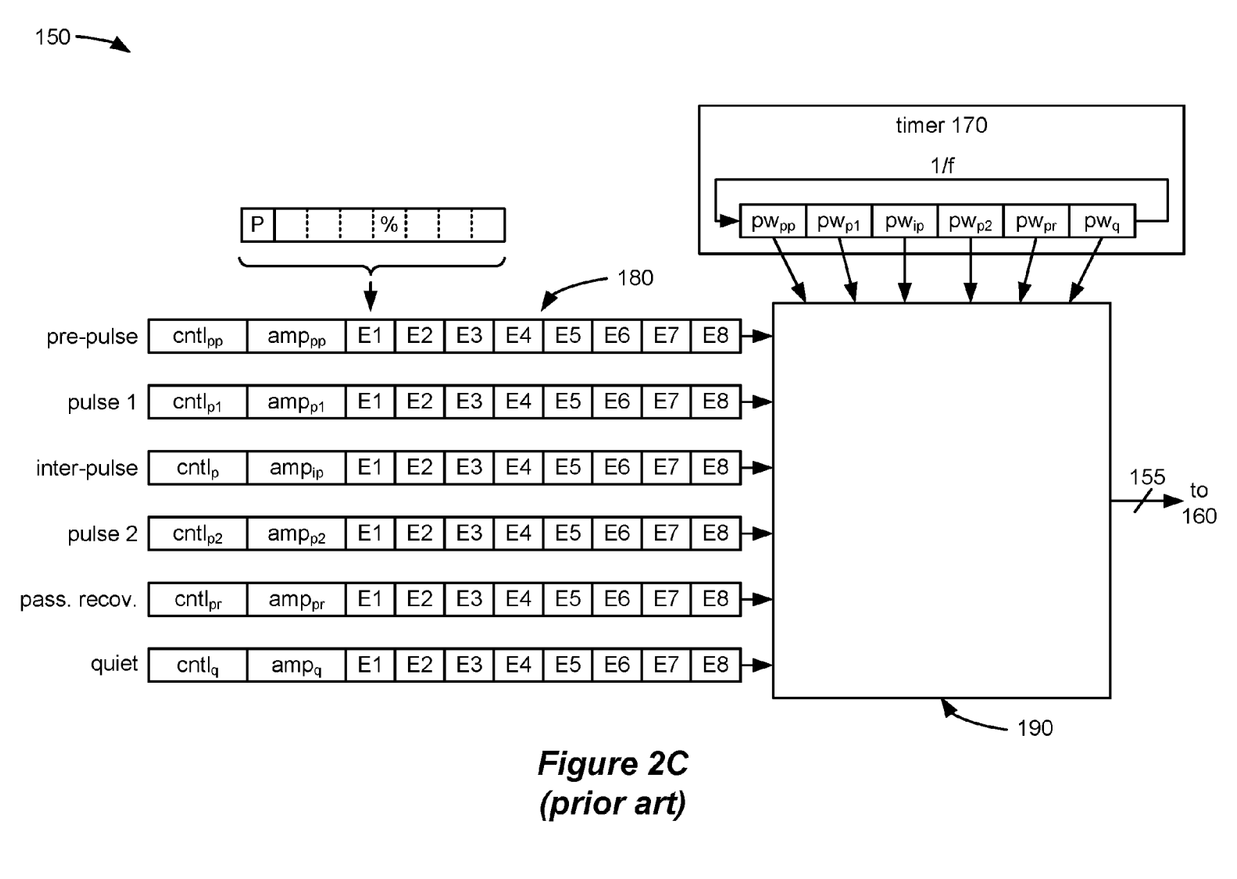

FIGS. 2A-2C illustrate typical pulses used in an IPG such as IPG 100, and the circuitry used to construct the pulses. Shown in FIG. 2A is a bi-phasic current pulse that issues a constant current of a given amplitude (amp) and pulse width (pw) between electrodes E1 and E2. Each pulse comprises a plurality of pulse phases, and is repeated in a period at a frequency f. The amplitude, pulse width, and frequency of the pulses can be patient-dependent, and may be arrived at by experimentation—i.e., based on what provides good therapy for the patient.

Circuitry for creating the pulses is shown in FIG. 2B and comprises timing channel circuitry 150 and stimulation circuitry 160 coupled via a digital bus 155. Stimulation circuitry 160 comprises a current source (PDAC) 83, a current sink (NDAC) 84, a switching matrix 85, and passive recovery switches 86, each of which will be explained subsequently. The PDAC 83 and NDAC 83 are so named because the amplitude of the analog current they source or sink is digitally controllable (hence, they are Digital-to-Analog Converters, or DACs), and because they are typically made from P-channel and N-channel transistors respectively.

Therapeutically meaningful phases of the example pulses in FIG. 2A will be explained first, starting with phase 1. In phase 1, electrode E1 acts as the cathode or sink for the current pulse, while electrode E2 acts of the anode or source of the current pulse. Thus, sourced current of the desired amplitude is issued from the PDAC 83 to E2 by closing an appropriate switch in the switching matrix 85, while sunk current of that same amplitude is drawn into the NDAC 84 from E1 by closing an appropriate switch in the switching matrix 85. This causes the current to flow from E2 to E1 through the patient's tissue (R). Notice that the pulses at E1 and E2 during phase 1 have the same amplitude (although of opposite polarities) and the same pulse width (pw), so that an excess of charge does not build up in the patient's tissue, R.

Because the pulse is bi-phasic, phase 1 is eventually followed by a second phase (phase 2), which in this example comprises a reversal of the polarity of the pulses at the two electrodes. Thus, in phase 2, E1 now acts as the anode, and E2 as the cathode, such that current now flows through the tissue R in the opposite direction. Phase 2, as is known, is useful to recover any excess charge that might have formed on any capacitances in the current path, such as the decoupling capacitors C1 and C2 coupled to electrodes E1 and E2 respectively (FIG. 2B). Connecting decoupling capacitors C1-CN to the electrodes E1-EN acts as a safety measure to prevent direct DC current injection into the patient. However, the storage of charge across such capacitors during the provision of the current is generally undesired. Reversing the current through those capacitances during phase 2 seeks to actively recover such stored charge, and thus phase 2 is sometimes referred to as an "active recovery" phase. To actively recover stored change in this fashion, it is preferable that the same amount of charge be passed in phase 2 as was passed in phase 1, which is most easily (and symmetrically) done by making the amplitude and pulse width of phase 2 equal to phase 1. However, one skilled will realize that symmetry between the pulses in phase 1 and phase 2 is not strictly necessary. For example, a pulse of lower amplitude and longer pulse width in phase 2 can also equate to the same amount of charge passed during phase 1. The polarity reversal of the pulses in phase 2 can be accomplished by the switching matrix 85, which in phase 2 will couple E1 to the PDAC 83, and E2 to the NDAC 84.

To ensure complete recovery of any stored charge, the active recovery phase (phase 2) can be followed by a passive recovery phase, as shown in FIG. 2A. In this passive recovery phase, the decoupling capacitors C1-C2 connected to previously-active electrodes E1 and E2 are shorted to a common potential via passive recovery switches 86 (FIG. 2B). In the example illustrated, this common potential, Vbat, comprises the voltage of the battery within the IPG 100, although other reference potentials could be used as well. Shorting the capacitors to Vbat effectively shorts them through the patient's tissue, and thus equilibrates any stored charge to assist in charge recovery. Some architectures may short only the previously-active electrodes by closing only the passive recovery switches 86 coupled to those electrodes, while other architectures will short all of the electrodes by closing all of the passive recovery switches 86.

Other pulse phases in each period are shown in FIG. 2A. Preceding pulse 1 is a pre-pulse phase, which is of low amplitude and long duration, and of opposite polarity to the phase 1 pulse that follows it. Experimentation suggests that the use of such a pre-pulse can help to assist in recruiting deeper nerves in an SCS application, although use of such a pre-pulse is not strictly necessary. An interpulse period between phases 1 and 2 of short duration allows the nerves to stabilize after being stimulated in phase 1. A quiet phase follows the passive recovery phase, and essentially acts as a waiting phase before the next period of pulses issues. The duration of the quite phase will depend on the durations of the phases that precede it in the period, as well as the frequency (f) at which the periods issue. There may be other pulses phases for different purposes; the phases shown in FIG. 2A are merely typical.

Referring again to FIG. 2B, the various phases of each period are controlled by timing channel circuitry 150, which digitally controls the various elements in the stimulation circuitry 160 via digital bus 155. There can be several timing channels circuitries 150 operating in a given IPG 100, defining other pulse sequences perhaps issued concurrently on other electrodes. However, only one timing channel circuitry 150 is illustrated for simplicity. The timing channel circuitry 150 receives and stores the data necessary to define the various phases in each pulse period. Such pulse parameters are provided to the timing channel circuitry 150 from control circuitry (e.g., a microcontroller) 110 via a digital bus 115. The control circuitry 110 in turn typically receives the pulse parameters wirelessly from an external device, such as an external controller. An external controller is typically a hand-held device usable by a patient or her clinician to select the pulse parameters, such as amplitude, pulse width, frequency, the electrodes to be used, and whether they are to act as anodes or cathodes.

FIG. 2C shows further details of the timing channel circuitry 150. Shown are a timer 170 and a register bank 180. The timer 170 stores the durations (pulse widths) of the phases in the period, while the register bank 180 stores control information, amplitude, active electrode, and electrode polarity information for the phases. Thus, a first register in the timer 170 stores the pulse width of the first pulse phase in the period (the pre-pulse ($pw_{pp}$) in the example of FIG. 2A), and the corresponding first register in the register bank 180 stores its control information ($cntl_{pp}$) amplitude ($amp_{pp}$), active electrode, and electrode polarities. A second register in the timer 170 stores the pulse width of the next pulse phase (phase 1 ($pw_{p1}$)), and the corresponding second register in the register bank 180 stores the control information ($cntl_{p1}$), amplitude ($amp_{p1}$), active electrode, and electrode polarity for phase 1. Data for subsequent pulse phases (interphase (ip), phase 2 (p2), passive recovery (pr), and quite (q)) are similarly stored in the timer 170 and register bank 180. The timer 170 may comprise a state machine in one example.

The control data in the registers ($cntl_x$) contains information necessary for proper control of the stimulation circuitry 160 for each phase. For example, during the passive recovery phase, the control data ($cntl_{pr}$) would instruct certain passive recovery switches 86 to close, and would disable the PDAC 83 and the NDAC 84. By contrast, during active phases, the control data would instruct the passive recovery switches 86 to open, and would enable the PDAC 83 and the NDAC 84.

Each register in the register bank 180 is, in one example, 96 bits in length, with the control data for the phase in the first 16 bits, the amplitude of the phase specified in the next 16 bits, followed by eight bits for each electrode. Each of the eight electrode bits in turn specifies the polarity (P) of the electrode in a single bit, with the remaining 7 bits specifying the percentage (%) of the amplitude that that electrode will receive. Thus, for the pre-pulse phase, the polarity bit P for E1 would be a '1', specifying that that electrode is to act as an anode, and thus will receive sourced current of the specified amplitude ($amp_{pp}$) from PDAC 83. The remaining seven bits for E1 would digitally represent 100%, indicating that E1 is to receive the entirety of the sourced current during the pre-pulse phase. (In more complicated examples, the sourced or sunk currents could be shared between electrodes, and thus smaller percentages would be indicated in the trailing seven bits for those electrodes). The polarity bit P for E2 during the pre-pulse phase would be a '0', specifying that that electrode is to act as a cathode, and thus will sink current as controlled by NDAC 84. Again, the remaining seven bits for E2 would digitally represent 100%, indicating that E2 is to receive the entirety of the sunk current during the pre-pulse phase.

The other registers in register bank 180 are programmed similarly for each phase. For example, all of the bits for E3-E8 in all of the registers would be set to zero for the example pulse phases of FIG. 2A, because those electrodes are not implicated. The amplitudes for the interphase ($amp_{ip}$), passive recovery ($amp_{pr}$), and quite ($amp_q$) phases would be set to zero as those phases do not require the PDAC 83 or NDAC 84 to actively issue any current.

The goal of the timing channel circuitry 150 is to send data from an appropriate register in the register bank 180 to the stimulation circuitry 160 at an appropriate point in time, and this occurs by control of the timer 170. As noted earlier, the pulse widths of the various phases are stored in the timer 170. Also stored at the timer is the frequency, f, the inverse of which (1/f) comprises the duration of each period. Knowing this period, the timer 170 can cycle through the durations of each of the pulse widths, and send the data in the register bank 180 to the stimulation circuitry 160 at the appropriate time. Thus, at the start of the period, the timer 170 enables a multiplexer 190 to pass the values stored in the first register for the pre-pulse to bus 155, which enables stimulation circuitry 160 to establish the pre-pulses at electrodes E1 and E2. After time $pw_{pp}$ has passed, the timer 170 now enables the multiplexer 190 to pass the values stored in the second register for phase 1 to the stimulation circuitry 160 to establish the phase 1 pulses at the electrodes. The other registers are similarly controlled by the timer 170 to send their data at appropriate times. This process of cycling through the various pulse phases continues, and eventually at the end of quite phase, i.e., at the end of $pw_q$, the timer 170 once again enables the pre-pulse data, and a new period of pulses is established.

This approach for controlling the stimulation circuitry 160 in accordance with each phase of the pulse period is adequate, but the inventors have found that this approach also suffers from certain shortcomings. A significant shortcoming is the lack of flexibility that the timing channel circuitry 150 provides to define more complex pulses. Take the pulse illustrated in FIG. 3 for example. This pulse generally contains the same phases as illustrated in FIG. 2A, but the currents specified during the therapeutically-meaningful phases (phases 1 and 2) are not constant currents, but instead comprise ramped currents. Experimentation suggests that such ramped pulses can be therapeutically useful in certain situations. Yet, the timing channel circuitry 150 as illustrated in FIG. 2C cannot direct the stimulation circuitry 160 to produce ramped pulses of this type, because only a constant amplitude can be specified for each phase in the register bank 180.

Figure 3:
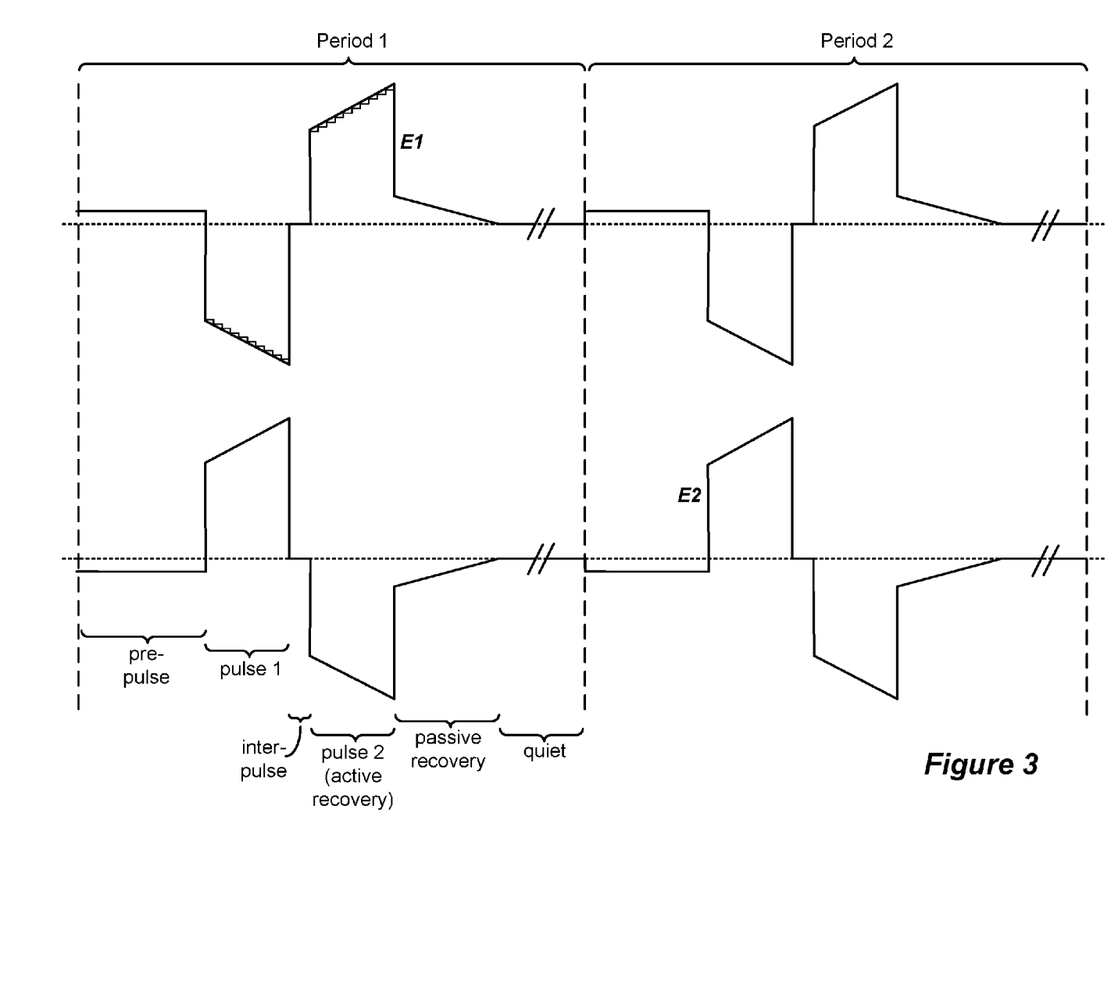
FIG. 3 illustrates a ramped pulse which is not easily handled by the timing channel circuitry of FIGS. 2B and 2C.

The inventors recognize that one could approximate a ramped pulse using the architecture of FIG. 2C by breaking the ramped pulse phases into a plurality of shorter phases, each with a constant current defining the ramp in a stair-wise fashion, as shown superimposed on phases 1 and 2 for electrode E1 in FIG. 3. However, this would require expanding the register bank 180 to accompany the increased number of phases in the period. Assume for example that to form a suitably-smooth ramp it would be necessary to parse both of phases 1 and 2 into ten smaller phases. The period would then comprise 24 different phases: the 20 phases needed in each of phases 1 and 2, the pre-pulse phase, the inter-pulse phase, the passive recovery phase, and the quiet phase. Because the register bank 180 must contain a register for each phase in the period, that bank 180 would then need 24 different registers. The 96 bits needed for each register in the bank 180 typically comprise flip flops, and so in this example 2304 (96*24) flip flops would be required, or more if the IPG 100 supports further numbers of electrodes. If the design of the integrated circuit is already fixed, and contains less than 24 registers, then the stair-wise approximation of the ramped pulses posited above simply could not be realized in that design. In short, the integrated circuit designer must either provide an undue number of area-intensive registers in register bank 180 to potentially handle the design of complex pulses in the future, or provide a limited number of such registers and forego the use of such complex pulses; neither option is desirable.

Furthermore, flip flops require significant layout area on the integrated circuitry in which the stimulation circuitry 160 is typically formed, which is undesirable. Further, the flip flops consume power when they are clocked, which can lead to complexity in gating the clocks to save power. The problem of excessive layout space is compounded by the fact that there may be more than one timing channel circuitry 150 operating in the device, as mentioned earlier. If the design of the integrated circuit is already fixed, and contains less than 24 registers, then the stair-wise approximation of the ramped pulses posited above simply could not be realized in that design. In short, the integrated circuit designer must either provide an undue number of area-intensive registers in register bank 180 to potentially handle the design of complex pulses in the future, or provide a limited number of such registers and forego the use of such complex pulses; neither option is desirable.

The multiplexer 190 also takes considerable layout and control. The multiplexer 190 must generally receive all 96 bits from each register, and so there are a total of 576 (96*6) bits being input to the multiplexer 190 in the example of FIG. 2C. The multiplexer 190 must in turn drive all of the 96 selected bits to the stimulation circuitry 160, which places power constraints on the system. Again, if there is more than one timing channel circuitry 150, such complexities and power issues are multiplied.

Also regrettable in the inventor's opinion is the fact that, depending on the particular phases in the pulse, certain of the register values in the register bank 180 will necessarily be irrelevant. For example, the amplitude and electrode values will necessarily be zero (or don't care values) for the illustrated interpulse, passive recovery, and quite phases. If the functions of the various phases are known in advance, the number of flip flops needed in the register bank (and thus the total number of inputs to the multiplexer 190) could be reduced. For example, if it is known in advance that the third register will always hold data for the interphase, the fifth register will always hold data for passive recovery, and the sixth register will always hold data for the quite phase, then those registers need not contain flip flops for holding the amplitude and electrode values. But reducing the number of flip flops in a given register limits future flexibility of the device. For example, if the registers just discussed above were made smaller, then those registers could not be used in the future for active stimulation phases.

A better solution is therefore needed to the aforementioned problems, and is provided by this disclosure.

DETAILED DESCRIPTION

Improved timing channel circuitry for controlling stimulation circuitry in an implantable stimulator is disclosed. The timing channel circuitry comprises a memory addressable by an address bus. Data for the various phases of a desired pulse are stored in the memory using different numbers of words, including, in one example, at least a command indicative of the number of words in the phase, a next address for the next phase stored in the memory, and a pulse width or duration of the current phase. Additional words stored in the memory for the current phase may include control data for the stimulation circuitry, pulse amplitude, and electrode data. The command data is used to address through the words in the current phase via the address bus, which words are sent by a data bus to a control register for the stimulation circuitry, which, depending on the data, may form a pulse phase at the electrodes. After the duration of the pulse width for the current phase has passed, the stored next address is output to the address bus to access the data for the next phase stored in the memory, and the process repeats to form a next pulse phase. The memory is physically smaller per bit than registers typically used to store data for each of the pulse phases, and therefore a larger number of pulse phases can be accommodated, which allows for the production of more complicated pulses. The data stored for each phase generally doesn't include unnecessary data, such as electrode data for phases not requiring stimulation, which further economizes storage of the data for the phases in the memory. Because data is sequentially sent one word at a time to the control register via the data bus, the complexity of multiplexing and control are reduced.

Figure 4:
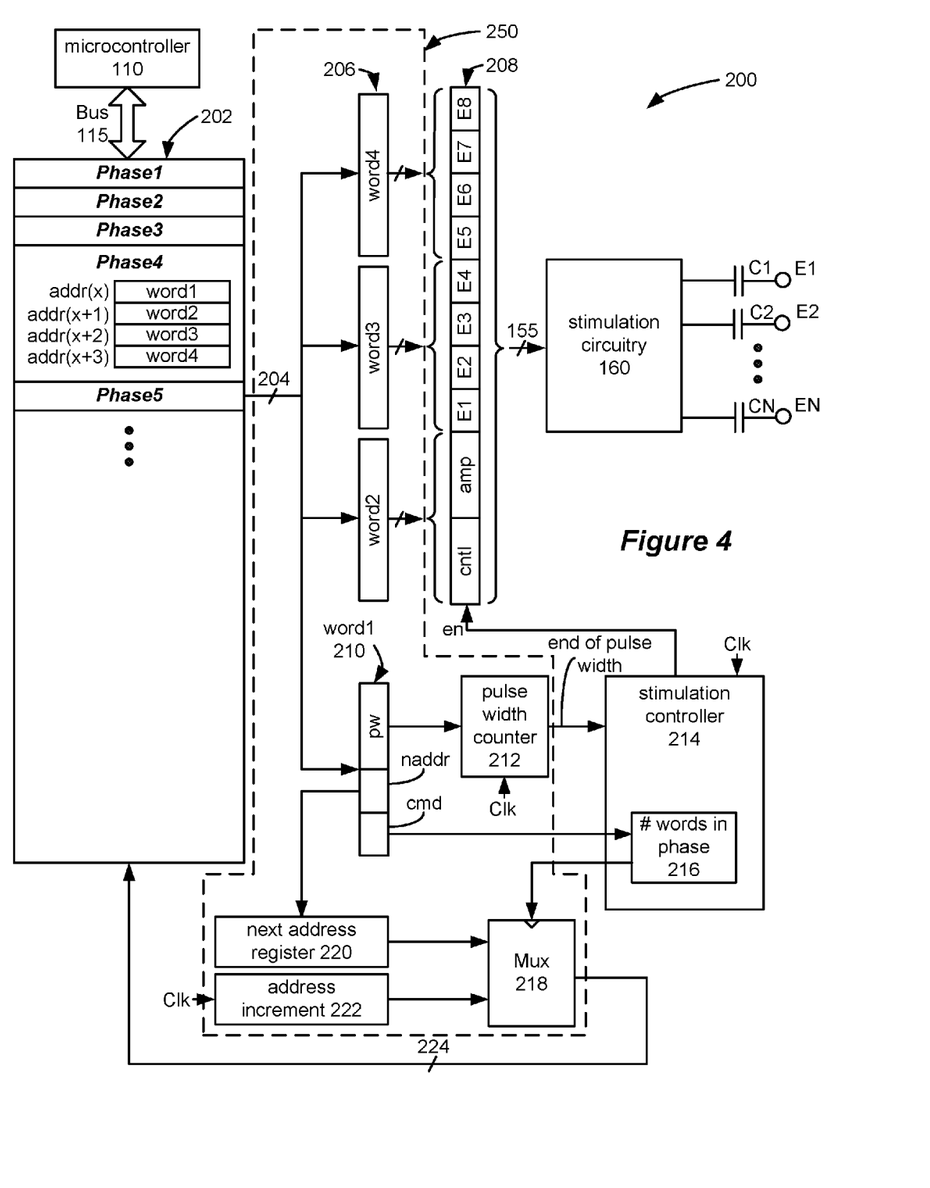
FIG. 4 illustrates improved timing channel circuitry employing a memory for holding the pulse parameters.

The new timing channel circuitry 200 for an IPG 100 is shown in a first example in FIG. 4. The various pulse parameters are stored in a dual-port memory 202, which may comprise a random-access memory for example. As one skilled in the art will understand, a dual-port memory can interface with two data and address buses which can run concurrently. As shown, bus 115 comprises a first address/data bus, and the pulse parameters are written from this bus 115 into the memory 202 from control circuitry 110. The second address/data bus is shown separately as a data bus 204 and an address bus 224 to better illustrate operation of the circuitry. The basic goal of the data bus 204 and address bus 224 is to read the stored pulse parameters from the memory 202 and to send them to stimulation circuitry 160 at the correct time to form the desired pulse phases.

Data for each of the pulse phases is stored in words in the memory 202 at different addresses, and each of the phases can comprise different numbers of words depending on the function of that phase. In the illustrated example, each word is 32-bits, and in example phase 4, four addresses (addr(x)-addr(x+3)) are shown holding four words of data (word1-word4) for that phase. When addressed, the data for each of these words is passed to one of registers 208 or 210 via the data bus 204. Specifically, data for the first word (word1) is passed to register 210, while data for the subsequent words (word2-word4) are passed to registers 206.

Each of the words has a particular pre-defined data structure and order in which they are stored in the memory 202 for each phase. The first word in each phase (word1) includes 8 bits defining a command (cmd), 8 bits defining an address in the memory 202 for a next phase ("next address" or naddr, described further below), and the pulse width (pw) for the phase. The next word in each phase (word2) includes 16 bits defining control for the stimulation circuitry 160 (cntl), and 16 bits defining the amplitude of the pulse for the phase (amp). The next words comprise electrode and polarity data of the pulse for the phase. Thus, word3 contains 8 bits for each of electrodes E1-E4, with each including a polarity bit and seven trailing bits defining the percentage of the amplitude that electrode receives, as discussed earlier in conjunction with the prior art. Word4 likewise contains similar data for electrodes E5-E8.

The data for each phase is written to the registers 206 and 210 by a stimulation controller 214, which operates as follows. When the first word in each phase is addressed (e.g., addr(x)), register 210 is populated with the command (cmd), the next address (naddr), and the pulse width (pw). The next address, naddr, is stored in next address register 220, which comprises the address in the memory 202 for the next pulse phase. For example, and assuming that the data for phase 4 is current being read, naddr would comprise the address in the memory 202 for the first word of phase 5. The command data (cmd) is sent to the stimulation controller 214. As will be explained in further detail with respect to FIG. 5, the command indicates the number of words stored for the phase, which can vary. The stimulation controller 214 determines this number of words (216) to control a multiplexer (mux) 218 to address the memory 202 via the address bus 224. For example, cmd in the example of FIG. 4 would inform the stimulation controller 214 that the current phase consists of three more words (word2-word4).

The current address (addr(x)) is incremented (222) in accordance with a system clock (Clk), which is also received by the stimulation controller 214. The mux 218 passes this incremented address to the address bus 224 as many times as necessary to address all of the remaining words in the phase. Thus, mux 218 in this example is controlled to pass addr(x+1)-addr(x+3) to the memory 202, which results in word2-word4 being sequentially loaded into registers 206 in subsequent cycles of the system clock, Clk. Such data, once latched, can be passed in unison to a control register 208 for the stimulation circuitry 160. Registers 206 and 208 can also be collapsed into a signal circuit. Regardless, once all words in the phase have been addressed and loaded, the stimulation controller 214 can enable (en) the control register 208 to issue the appropriate data via bus 155 to the stimulation circuitry 160 to form the appropriate pulse phase (phase 4) at the electrodes. Notice that the data sent to the stimulation circuitry 160 via bus 155 is the same (cntl, amp, E1-E8) as was used in the prior art circuitry (FIG. 2C), and as a result, stimulation circuitry 160 can remain unchanged.

Once the pulse phase is established at the stimulation circuitry 160, the stimulation controller 214 waits to take further action until the duration of that phase has elapsed. This occurs in the illustrated example by use of a pulse width counter 212, which receives the pulse width (pw) of the current phase from register 210. As the period of the system clock Clk is known, the counter 212 can know when the duration of the pulse width has expired, at which time it issues an end of pulse width command to the stimulation controller 214. When this occurs, the stimulation controller 214 now controls the mux 218 to pass to the address bus 224 the next address (naddr) that had been stored in register 210 previously. As discussed earlier, that next address comprises the address of the first word in the next phase (phase 5).

When the memory 202 receives this first address of the next phase (phase 5), the process described above repeats: a new word1 for phase 5 is loaded into the register 210, including a next address (for phase 6), a new command (which informs concerning the number of words stored for phase 5), and a new pulse width (for phase 5). Mux 218 under control of the stimulation controller 214 provides addresses for the remaining words in phase 5 as assisted by the address incrementer 222. These new addresses populate registers 206 with the appropriate data for phase 5, which data is then passed to stimulation circuitry 160 to establish the phase 5 pulse, etc.

The system clock, Clk, is typically on the order of a Megahertz or more, and so the period of the system clock (less than a microsecond) is typically small compared to the durations of the pulse widths of the various pulse phases (on the order of tens of microseconds or more). As a result, the timing channel circuitry 200 essentially works instantaneously to provide the pulse parameters to the stimulation circuitry 160 from the memory 202.

Figure 5:
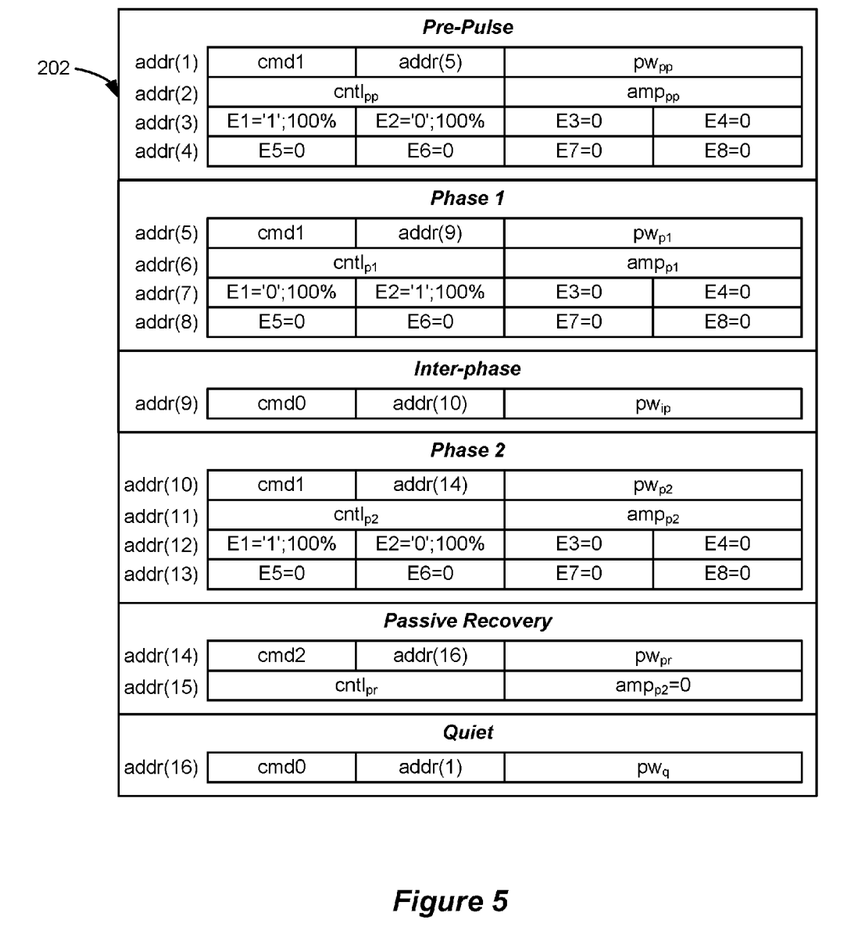
FIG. 5 illustrates how data is populated in the memory to form the pulses of FIG. 2A.

FIG. 5 shows further details of the memory 202 and how it can be populated to form the example pulses shown in FIG. 2A. As discussed earlier, the pulses in FIG. 2A contain six phases, and the data for each of the phases are stored as shown. Active phases requiring the PDAC 83 and NDAC 84 to generate pulses (such as pre-pulse, phase 1, and phase 2) are denoted as such by command cmd1 in their first words. This command informs the stimulation controller 214 that there are three additional words associated with these phases, so that addressing can be controlled as discussed above. These additional words, as noted earlier, include control data, amplitudes, and electrode polarities and percentages.

Notice that the next address stored in the first word of each phase points to the first word in the next phase, which allows the stimulation controller 214 to addresses such next phase as described above. Thus, the next address stored for the pre-pulse phase (in addr(1)) points to the first address in phase 1 (addr(5)). The next address stored for phase 1 (in addr(5)) points to the first address for the inter-phase (addr (9)), and so on.

Phases requiring only delay but not active generation of currents, such as the inter-phase and the quiet phase, are denoted by command cmd0 in their first words. Because such phases do not impact stimulation circuitry 160, they may be stored in memory 202 and interpreted by the stimulation controller 214 as only a single word, including their durations, and the next address.

The passive recovery phase is denoted by command cmd2 in its first word, which requires two words in the illustrated example. This phase does not require electrode data (as found in word3 and word4 of the active phases), but does require control data ($cntl_{pr}$) to inform the stimulation circuitry 160 to close certain of the passive recovery switches 86 (FIG. 2B). Because passive recovery is not associated with an amplitude, that field in word2 can be populated with don't-care values, or simply set to zero.

Other commands (cmd) are possible, but are not illustrated. For example, other commands may instruct stimulation circuitry 160 to measure the voltages at the electrodes either during stimulation or during periods of no stimulation. Such measurements can be useful for taking impedance measurements (e.g., for checking the continuity of the electrodes), for setting the power supply voltage (V+) for the DACs 83 and 84 (FIG. 2B), or for monitoring electrical activity in the tissue of the patient (such as seizures in a deep brain stimulation application). See, e.g., U.S. Pat. Nos. 7,444,190 and 6,993,384. Other commands may cause stimulation circuitry 160 to burst the currents at the electrodes, i.e., by fractionalizing the pulses into higher-frequency micropulses. See, e.g., U.S. Pat. No. 7,890,182. Such other commands may require different numbers of words in memory 202, and different control data (cntl), depending on what aspects of stimulation circuitry 160 require control.

Figure 6:
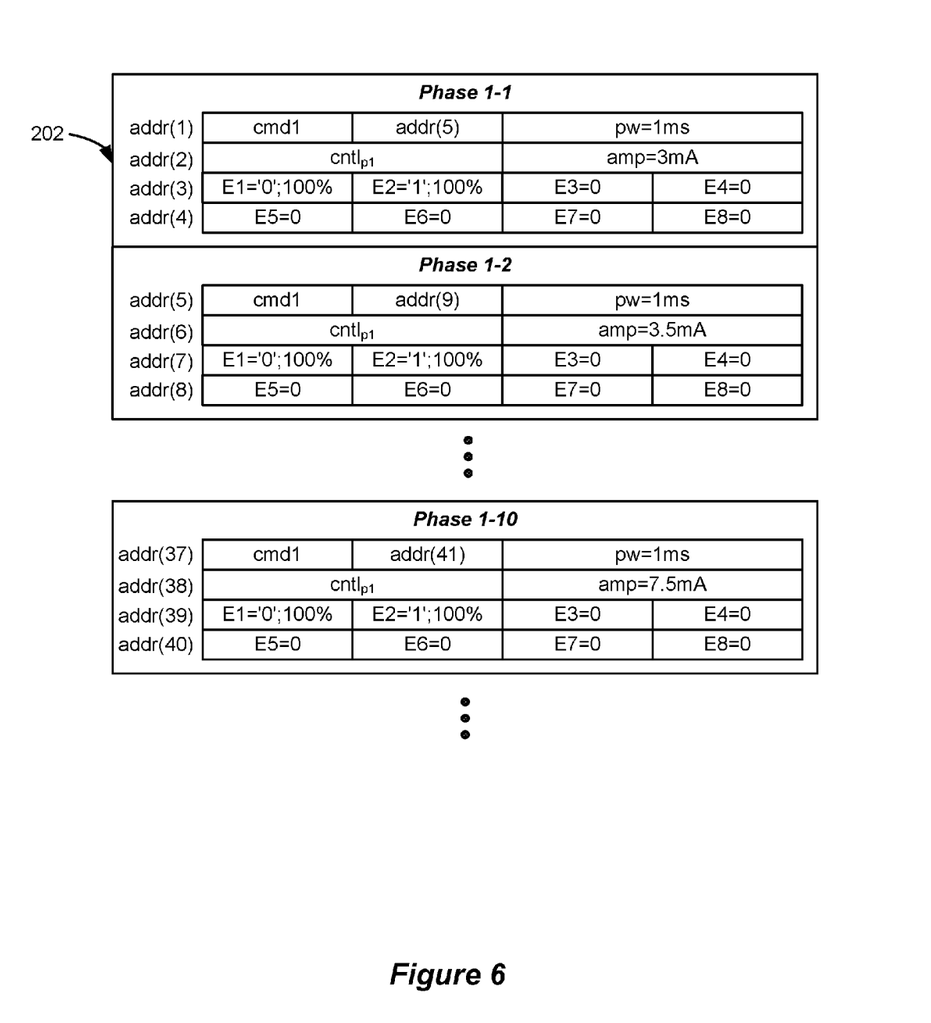
FIG. 6 illustrates how data is populated in the memory to form the ramp pulses of FIG. 3.

With an example of the improved timing channel circuitry 200 understood, advantages over the prior art discussed in the Background can be appreciated. First, the memory cells in memory 202 are generally smaller than the flip flops used in the register bank 180 of the prior art (180), and thus a greater number of memory locations can be provided to hold and define the pulse parameters. As such, memory 202 provides greater flexibility to produce pulses with more-complex shapes. Take the ramping pulse of FIG. 3 for instance, which as noted earlier was not feasible to produce in the prior art without an undue number of registers in register bank 180. Such ramped pulses can be more easily stored in memory 202, as shown in FIG. 6, which shows the data for a ramped phase 1 pulse. The ramped pulse increases from 3 mA to 7.5 mA over a duration of 10 ms, and so 10 smaller phases of 1 ms (phases 1-1 to 1-10) increment the amplitude by 0.5 mA each time. The added flexibility provided by the increased number of memory locations in memory 202 allows for the provision of pulses of many shapes. Clinicians are constantly experimenting with finding pulse shapes that will provide patients better therapy, and so such flexibility enables such experimentation.

Additionally, timing channel circuitry 200 does not require discrete multiplexers (190, FIG. 2C) to route pulse parameters to the stimulation circuitry 160, which as noted must handle and drive hundreds of signals, and take up significant layout area and power to drive. Because the data for each pulse phase is divided into 32-bit words, data bus 204 need only be 32 bits wide in the illustrated example, which is easier to drive and control.

Another significant benefit to timing channel circuitry 200 is that data stored for each phase can be reduced to eliminate irrelevant values. As noted earlier, in the prior art, all phases generally require a complete register in the register bank 180 (FIG. 2C) (assuming certain dedicated registers are not shortened, as discussed earlier), even if a given phase does not require use of all values in the register, such as the amplitude and electrode values for the interpulse, passive recovery, and quite phases. Dividing the data for each phase into words, and using commands to define the number of words for each phase, allows the data for certain phases to be narrowed from the 96 bits otherwise specified for the registers in the register bank 180. As discussed earlier with respect to FIG. 5, inactive phases (inter-phase, quite) require the storage of only one word (32 bits) in the memory 202; passive recovery only requires two words (64 bits). The efficiency of reducing the phase data in this manner becomes more substantial in IPG architectures with even greater numbers of electrodes. However, it is not strictly to reduce the phase data in this way, and instead every pulse phase could comprise a set number of words in the memory 202, even if some of this data is not useful for a given phase. In that circumstance, the address for the next phase would be known in advance, and it therefore would not be required to store the next address in word1, as illustrated earlier.

Figure 7:
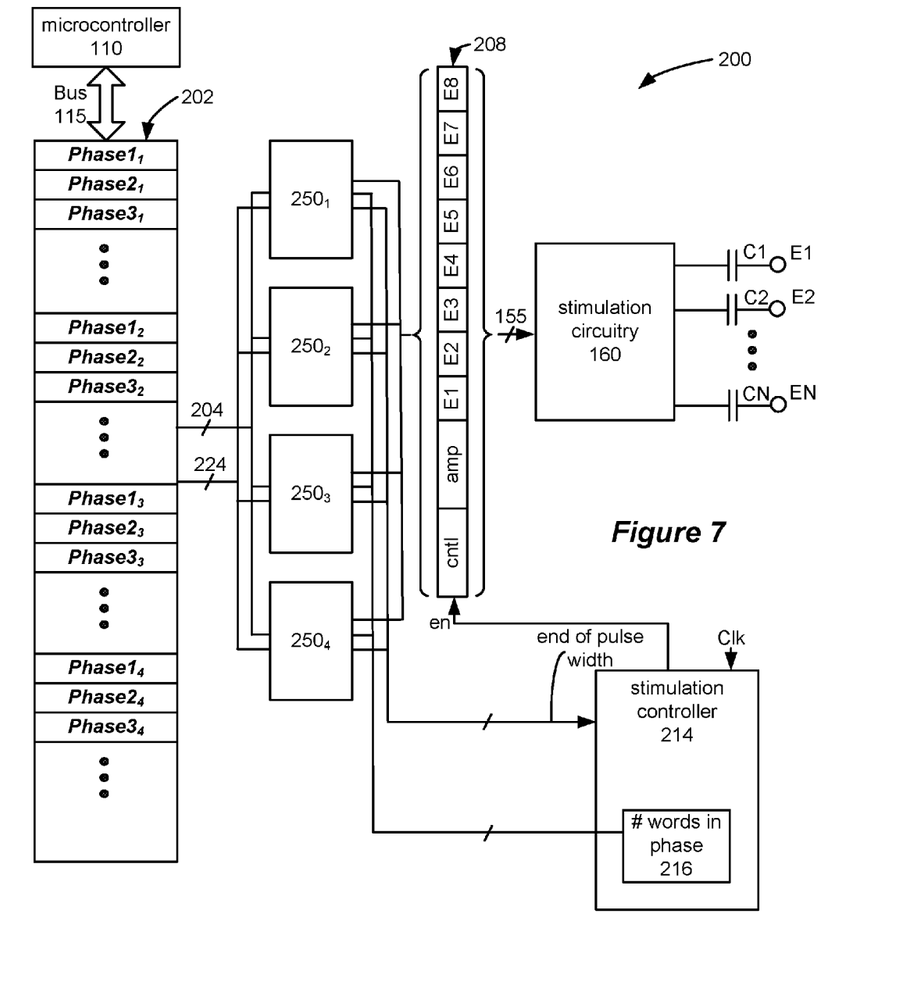
FIG. 7 illustrates the extension of the improved timing channel circuitry to multiple timing channels.

Benefits to the disclosed circuitry are multiplied when timing channel circuitry 200 is extended to support more than one timing channel, and the extension to four timing channels is illustrated in FIG. 7. As shown, only one memory 202 is needed to hold all of the pulse parameters for the timing channels 150, each of which is denoted by a subscript. Certain circuitry 250 (shown in the dotted lined box in FIG. 4) is repeated for each timing channel, but other circuitry, such as the control register 208 and stimulation controller 214, can be shared by each timing channel.

Modifications may be made to timing channel circuitry 200. For example, memory 202 need not be a dual-port RAM supporting two address/data buses: bus 115 that communicates with the control circuitry 110 and buses 204/224 that communicate with the stimulation circuitry 160. Instead, communications on a single address/data bus could be time multiplexed. Additionally, the data bus 204 and address bus 224 could also comprise a single, time-multiplexed bus.

Memory 202 preferably comprises random access memory, such as static or dynamic random access memory. However, programmable/erasable non-volatile memory could be used as well, such as Flash memory. While programming and erasing require additional overhead if the pulse parameters are changed, such therapy changes do not occur frequently, and erasure and re-programming are suitably quick from the patient's perspective.

Timing channel circuitry 200 can be implemented in the same integrated circuit upon which the stimulation circuitry 160 is normally fabricated, but can also be discrete therefrom. Although shown in FIG. 4 as discrete circuit hardware blocks, many of the aspects of the circuitry can be implemented in software or firmware as well, as one skilled in the art will appreciate.

Timing channel circuitry 200 can be scaled in many different ways. Additional electrodes can be supported beyond the eight illustrated. For example, if IPG 100 contains 16 electrodes, additional words can be included in the memory 202 for each phase requiring electrode data, such as the active phases. Or, the width of the memory 202 can be increased to accommodate longer 64-bit words for example.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An implantable stimulator device, comprising:
   a memory configured to store pulse parameters for a periodic pulse, wherein each pulse comprises a plurality of sequential pulse phases each with a duration;
   stimulation circuitry configured to sequentially form the pulse phases at electrodes for stimulating a patient's tissue, wherein the memory is addressable via an address bus to sequentially provide via a data bus the pulse parameters to the stimulation circuitry,
   wherein the pulse parameters for at least one of the pulse phases is stored in a plurality of addresses in the memory, and
   wherein the pulse parameters comprise amplitude data, active electrode data, and electrode polarity data for at least some of the plurality of pulse phases.

2. The implantable stimulator device of claim 1, wherein the pulse parameters for the plurality of pulse phases do not comprise the same number of addresses in the memory.

3. The implantable stimulator device of claim 1, wherein a first address in the memory for the pulse parameters for each of the plurality of pulse phases comprises a pre-defined data structure, wherein the first address comprises the duration for each pulse phase.

4. The implantable stimulator device of claim 3, wherein the first address further comprises a command indicative of the number of addresses in which pulse parameters are stored in the memory for each pulse phase.

5. The implantable stimulator device of claim 4, wherein the first address further comprises an address in the memory for a subsequent pulse phase.

6. The implantable stimulator device of claim 1, further comprising a clock, wherein the plurality of addresses for each of the at least one pulse phases are sequentially read out of the memory in accordance with the clock.

7. The implantable stimulator device of claim 1, wherein the pulse parameters do not comprise amplitude data, active electrode data, or electrode polarity data for at least some of the plurality of pulse phases.

8. The implantable stimulator device of claim 1, wherein at least some of the pulse parameters for each of the at least one pulse phases are provided to a first register, wherein the first register stores information for addressing the memory and for timing each of the plurality of phases.

9. The implantable stimulator device of claim 1, wherein at least some of the pulse parameters for each of the at least one pulse phases are provided to a second register, wherein the second register provides the at least some of the pulse parameters to the stimulation circuitry in parallel.

10. The implantable stimulator device of claim 1, wherein the plurality of pulse phases are selected from the group consisting of an active phase that actively provides current at the electrodes, a recovery phase for collecting stored charge but which does not actively provide current at the electrodes, and a quite phase that does not actively provide current at the electrodes.

11. An implantable stimulator device, comprising:
    a memory configured to store pulse parameters for a periodic pulse, wherein each pulse comprises a plurality of sequential pulse phases each with a duration; and
    stimulation circuitry configured to sequentially form the pulse phases at electrodes for stimulating a patient's tissue, wherein the memory is addressable via an address bus to sequentially provide via a data bus the pulse parameters to the stimulation circuitry,
    wherein the pulse parameters for at least one of the pulse phases is stored in a plurality of addresses in the memory,
    wherein a first address in the memory for the pulse parameters for each of the plurality of pulse phases comprises a pre-defined data structure.

12. The implantable stimulator device of claim 11, wherein the pulse parameters for the plurality of pulse phases do not comprise the same number of addresses in the memory.

13. The implantable stimulator device of claim 11, wherein the pulse parameters comprise amplitude data, active electrode data, and electrode polarity data for at least some of the plurality of pulse phases.

14. The implantable stimulator device of claim 11, further comprising a clock, wherein the plurality of addresses for each pulse phase are sequentially read out of the memory in accordance with the clock.

15. The implantable stimulator device of claim 11, wherein the plurality of pulse phases are selected from the group consisting of an active phase that actively provides current at the electrodes, a recovery phase for collecting stored charge but which does not actively provide current at the electrodes, and a quite phase that does not actively provide current at the electrodes.

16. An implantable stimulator device, comprising:
    a memory configured to store pulse parameters for a periodic pulse, wherein each pulse comprises a plurality of sequential pulse phases each with a duration; and
    stimulation circuitry configured to sequentially form the pulse phases at electrodes for stimulating a patient's tissue, wherein the memory is addressable via an address bus to sequentially provide via a data bus the pulse parameters to the stimulation circuitry,
    wherein the pulse parameters for at least one of the pulse phases is stored in a plurality of addresses in the memory,
    wherein the plurality of pulse phases comprise an active phase that actively provides current at the electrodes, a recovery phase for collecting stored charge but which does not actively provide current at the electrodes, and a quite phase that does not actively provide current at the electrodes,
    wherein the active phase, the recovery phase, and the quite phase are stored in different numbers of addresses in the memory.

17. The implantable stimulator device of claim 16, wherein the pulse parameters for the plurality of pulse phases do not comprise the same number of addresses in the memory.

18. The implantable stimulator device of claim 16, wherein the pulse parameters comprise amplitude data, active electrode data, and electrode polarity data for at least some of the plurality of pulse phases.

19. The implantable stimulator device of claim 16, further comprising a clock, wherein the plurality of addresses for each pulse phase are sequentially read out of the memory in accordance with the clock.

* * * * *